(12) United States Patent
Russie et al.

(10) Patent No.: US 7,623,921 B2
(45) Date of Patent: *Nov. 24, 2009

(54) SYSTEM AND METHOD FOR VERIFYING CAPTURE IN A MULTI-SITE PACEMAKER

(75) Inventors: Renold J. Russie, New Brighton, MN (US); Qingsheng Zhu, Little Canada, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 267 days.

This patent is subject to a terminal disclaimer.

(21) Appl. No.: 11/210,143

(22) Filed: Aug. 23, 2005

(65) Prior Publication Data

US 2006/0069411 A1  Mar. 30, 2006

Related U.S. Application Data

(63) Continuation of application No. 10/646,476, filed on Aug. 22, 2003, now Pat. No. 6,963,775, which is a continuation of application No. 09/540,388, filed on Mar. 31, 2000, now Pat. No. 6,615,089.

(51) Int. Cl.
*A61N 1/00* (2006.01)
(52) U.S. Cl. ...................................................... 607/28
(58) Field of Classification Search ............. 607/27–30, 607/9, 21; 700/82
See application file for complete search history.

(56) References Cited

U.S. PATENT DOCUMENTS

| | | | |
|---|---|---|---|
| 3,949,758 A * | 4/1976 | Jirak | ........................... 607/28 |
| 4,114,627 A | 9/1978 | Lewyn et al. | |
| 4,236,524 A * | 12/1980 | Powell et al. | ................. 607/30 |
| 4,928,688 A | 5/1990 | Mower | |
| 5,222,493 A | 6/1993 | Sholder | |
| 5,324,310 A | 6/1994 | Greeninger et al. | |
| 5,331,966 A | 7/1994 | Bennett et al. | |
| 5,431,693 A | 7/1995 | Schroeppel | |
| 5,443,485 A | 8/1995 | Housworth et al. | |
| 5,571,144 A | 11/1996 | Schroeppel | |
| 5,601,615 A | 2/1997 | Markowitz et al. | |
| 5,609,611 A | 3/1997 | Bolz et al. | |
| 5,683,431 A | 11/1997 | Wang | |
| 5,718,720 A | 2/1998 | Prutchi et al. | |
| 5,766,225 A | 6/1998 | Kramm | |
| 5,792,203 A | 8/1998 | Schroeppel | |
| 5,843,136 A | 12/1998 | Zhu et al. | |
| 5,861,012 A | 1/1999 | Stroebel | |
| 5,873,898 A | 2/1999 | Hemming et al. | |

(Continued)

FOREIGN PATENT DOCUMENTS

WO    WO-99/29368    6/1999

*Primary Examiner*—George Manuel
(74) *Attorney, Agent, or Firm*—Schwegman, Lundberg & Woessner, P.A.

(57) ABSTRACT

An apparatus and method for verifying capture by a selected pacing electrode in a multi-site pacemaker. A switching circuit switches the input of an evoked response sensing channel to an unselected electrode. A pacing pulse is then output by the selected electrode, and the presence or absence of capture is determined from the output of the evoked response sensing channel. In one embodiment, a backup pacing pulse is output by an unselected electrode if a loss of capture is detected.

20 Claims, 3 Drawing Sheets

U.S. PATENT DOCUMENTS

| | | |
|---|---|---|
| 5,935,160 A | 8/1999 | Auricchio et al. |
| 6,128,535 A | 10/2000 | Maarse |
| 6,169,921 B1 | 1/2001 | KenKnight et al. |
| 6,345,201 B1 | 2/2002 | Sloman et al. |
| 6,456,879 B1 | 9/2002 | Weinberg |
| 6,611,712 B2 | 8/2003 | Spinelli et al. |
| 6,615,089 B1 | 9/2003 | Russie et al. |

* cited by examiner

SYSTEM AND METHOD FOR VERIFYING CAPTURE IN A MULTI-SITE PACEMAKER

CROSS-REFERENCE TO RELATED APPLICATION

This application is a continuation of U.S. patent application Ser. No. 10/646,476, filed on Aug. 22, 2003, now issued as U.S. Pat. No. 6,963,775, which is a continuation of U.S. patent application Ser. No. 09/540,388, filed on Mar. 31, 2000, now issued as U.S. Pat. No. 6,615,089, the specification of which is incorporated herein by reference.

FIELD OF THE INVENTION

This invention pertains to cardiac pacemakers and, in particular, to systems and methods for monitoring the effects of pacing and adjusting pacing parameters in accordance therewith.

BACKGROUND

Cardiac pacemakers are medical devices, usually implantable, that provide electrical stimulation in the form of pacing pulses to selected chambers of the heart (e.g., the right atrium and/or the right ventricle). Pacemakers typically have a programmable electronic controller that causes the pacing pulses to be output in response to lapsed time intervals and sensed electrical activity (i.e., intrinsic heart beats). Implantable pacemakers sense intrinsic cardiac electrical activity by means of internal electrodes disposed near the chamber to be sensed, with the depolarization waves associated with contractions of the atria and ventricles referred to as P waves and R waves, respectively. In order to cause such a contraction in the absence of intrinsic activity, a pacing pulse (referred to as an A-pace or V-pace in the case of an atrium or ventricle, respectively) with energy above a certain pacing threshold is delivered to the chamber.

Most pacemakers are programmed to operate in a so-called demand mode (a.k.a., synchronous mode), where a pacing pulse is delivered to a heart chamber during a cardiac cycle only when no intrinsic beat by the chamber is detected. An escape interval is defined for each paced chamber, which is the minimum time interval in which a beat must be detected before a pace will be delivered. The ventricular escape interval thus defines the minimum rate at which the pacemaker will allow the heart to beat, sometimes referred to as the lower rate limit. If functioning properly, the pacemaker in this manner makes up for a heart's inability to pace itself at an appropriate rhythm.

In order for a pacemaker to control the heart rate in the manner described above, the paces delivered by the device must achieve "capture," which refers to causing sufficient depolarization of the myocardium that a propagating wave of excitation and contraction result (i.e., a heart beat). A pacing pulse that does not capture the heart is thus an ineffective pulse. This not only wastes energy from the limited energy resources (battery) of pacemaker, but can have deleterious physiological effects as well, since a demand pacemaker that is not achieving capture is not performing its function in enforcing a minimum heart rate. A number of factors can determine whether a given pacing pulse will achieve capture, but the principal factor of concern here is the energy of the pulse, which is a function of the pulse's amplitude and duration or width. Programmable pacemakers enable the amplitude and pulse width of pacing pulses to be adjusted, along with other parameters. It is therefore desirable to perform a capture verification test at selected times in order to ascertain whether capture is being achieved by a pacemaker so that such parameters can be adjusted if needed.

A common technique used to determine if capture is present during a given cardiac cycle is to look for an "evoked response" immediately following a pacing pulse. The evoked response is the wave of depolarization that results from the pacing pulse and evidences that the paced chamber has responded appropriately and contracted. By detecting the evoked P-wave or evoked R-wave, the pacemaker is able to detect whether the pacing pulse (A-pulse or V-pulse) was effective in capturing the heart, that is, causing a contraction in the respective heart chamber. Capture verification can be performed in the clinical setting, with the clinician then adjusting pacing parameters so that the heart is reliably paced. It is desirable, however, for the pacemaker itself to be capable of verifying capture so that loss of capture can be detected when it occurs with pacing parameters then adjusted automatically, a function known as autocapture. An autocapture function provides the pacemaker with extended longevity, greater ease of use, and greater patient safety. In order for a pacemaker to detect whether an evoked P-wave or an evoked R-wave occurs immediately following an A-pulse or a V-pulse, a period of time, referred to as the atrial capture detection window or the ventricular capture detection window, respectively, starts after the generation of the pulse. Sensing channels are normally rendered refractory (i.e., insensitive) for a specified time period immediately following a pace in order to prevent the pacemaker from mistaking a pacing pulse or afterpotential for an intrinsic beat. This is done by the pacemaker controller ignoring sensed events during the refractory intervals, which are defined for both atrial and ventricular sensing channels and with respect to both atrial and ventricular pacing events. Furthermore, a separate period that overlaps the early part of a refractory interval is also defined, called a blanking interval during which the sense amplifiers are blocked from receiving input in order to prevent their saturation during a pacing pulse. If the same sensing channels are used for both sensing intrinsic activity and evoked responses, the capture detection window must therefore be defined as a period that supercedes the normal refractory period so that the sensing circuitry within the pacemaker becomes sensitive to an evoked P-wave or R-wave.

In certain devices, capture verification is performed by delivering a pacing pulse and attempting to sense an evoked response using the same electrode. Such a technique suffers from a number of problems, however. One is the induced polarization that builds up on an electrode after a pacing pulse which interferes with sensing by the electrode. Another is that an evoked response is a wave of depolarization that necessarily moves away from a pacing electrode responsible for the depolarization. Since such a wave of depolarization causes an electric field equivalent to a moving dipole disk, the potential resulting from that field is best sensed by an electrode that lies in the path of the wave. Also, if a backup pacing pulse is to be delivered, using the same pulse generator that produced the non-capturing pacing pulse for this purpose means that the output capacitor of the pulse generator must be recharged before another pace can be delivered, which takes some time.

SUMMARY OF THE INVENTION

The present invention is an apparatus and method for verifying capture by a pacing electrode in a multi-site pacemaker. Such a pacemaker includes a plurality of sensing/pacing channels, with each such channel comprising an electrode for disposing near a right or left chamber of the heart, a pulse generator for outputting pacing pulses, and a sense amplifier for detecting sense signals. A controller controls the operation of the pulse generators in response to sensed events and lapsed time intervals and in accordance with a programmed pacing mode. The controller is programmed to test a selected sensing/channel for presence or loss of capture by performing a capture verification test at a selected time. A capture verification test on a selected pacing electrode is performed by sensing whether an evoked response occurs during a capture detection window period following the output of a pacing pulse through the test electrode. The programming may dictate that a capture verification test is performed at periodic intervals or in response to a command received via a telemetry interface from an external programmer.

In accordance with the invention, a dedicated evoked response sensing channel is provided which includes a sense amplifier for sensing an evoked response generated after a pacing pulse. Also, a switching circuit is provided that switches the input of the evoked response sensing channel to a selected electrode of the sensing/pacing channels before the capture verification test is performed. Preferably, the input of the evoked response sensing channel is switched to an electrode of a sensing/pacing channel other than the channel being tested during a capture verification test. The sense amplifier of the evoked response sensing channel is then blanked during the capture verification test for a specified blanking period following a pacing pulse output by the tested sensing/pacing channel, and the blanking period is followed by a capture detection window during which an evoked response may be sensed.

Another advantage of using a dedicated sense amplifier for detecting evoked responses to paces is that a bandpass filter with a wide passband can be used. Sensing/pacing channels used for sensing intrinsic cardiac activity employ filters with narrow passbands in order to best detect the signals they are designed to sense. A typical signal due to an evoked response that is processed through such a narrow passband filter, however, results in a waveform that makes detection of the evoked response more difficult. Thus, the sensing amplifier of the dedicated evoked response sensing channel is preferably one with a wide passband.

Also in accordance with the invention, the controller is programmed to output a backup pacing pulse through a sensing/pacing channel if loss of capture is detected during a capture verification test. In the event no evoked response is detected by the pacemaker during the atrial or ventricular capture detection window, and if the pacemaker is operating in an autocapture mode, the pacemaker delivers a backup pacing pulse some time after the capture detection window expires. The backup pacing pulse may be an A-pulse or V-pulse of greater amplitude, pulse width or both than the initial atrial or ventricular stimulation pulse. The backup pacing pulse is designed to capture the heart when the initial, lower amplitude and/or lower pulse width stimulation pulse was unable to do so. The backup pacing pulse may be output through a sensing/pacing channel other than the channel being tested during the capture verification test. In certain embodiments, the backup pacing channel uses the same electrode as the evoked response sensing channel. In a pacemaker that provides multi-site pacing, such as a biventricular pacemaker, normal pacing is preferably suspended in the sensing/pacing channel used to sense the evoked response and provide backup pacing.

DETAILED DESCRIPTION OF THE INVENTION

Figure 1:
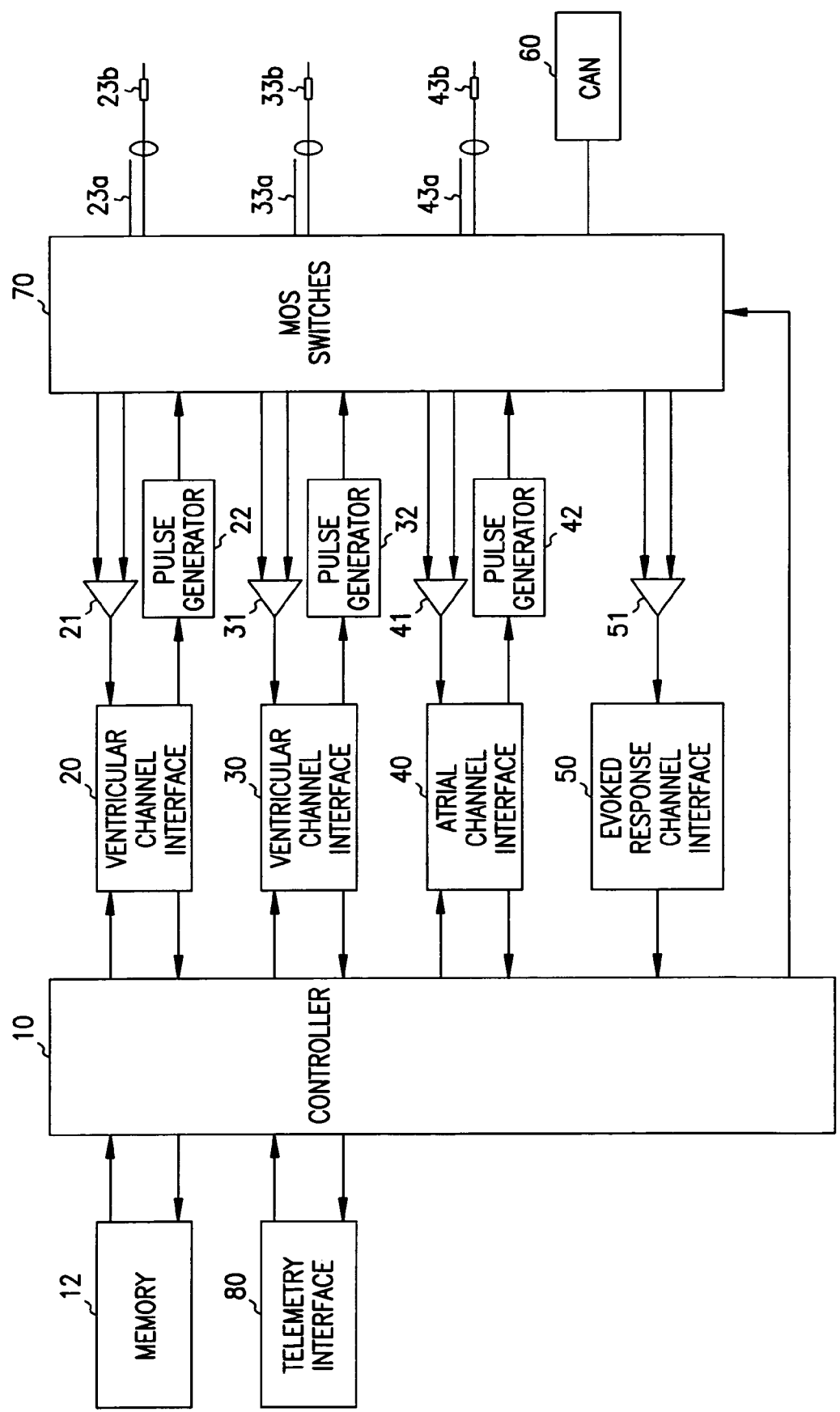
FIG. 1 is a block diagram of a multi-site pacemaker in accordance with the present invention.

Pacemakers have been constructed for delivering pacing pulses to multiple ventricular or atrial sites, including so-called biventricular pacemakers where pacing pulses are delivered to both ventricles by separate electrodes during a cardiac cycle. (See, e.g., U.S. Pat. Nos. 5,792,203 and 4,928,688, referred to herein as the '203 and '688 patents, which are hereby incorporated by reference.) Biventricular pacemakers have been found to be useful in treating congestive heart failure (CHF), a clinical syndrome in which an abnormality of cardiac function causes cardiac output to fall below a level adequate to meet the metabolic demand of peripheral tissues. CHF can be due to a variety of etiologies, with ischemic heart disease being the most common. Some CHF patients suffer from some degree of AV block such that their cardiac output can be improved by synchronizing atrial and ventricular contractions with dual-chamber pacing using a short programmed AV delay time. It has also been shown, however, that some CHF patients suffer from intraventricular conduction defects (a.k.a. bundle branch blocks). The cardiac outputs of these can be increased by improving the synchronization of right and left ventricular contractions with biventricular pacing.

One type of multi-site pacing involves fixing two or more pacing electrodes to separate sites of the same heart chamber, either an atrium or a ventricle. For example, one electrode may be fixed to the apical region of either the right or left ventricle with the other electrode fixed to a basal region of the same ventricle. In the case of the left ventricle, this may be most easily accomplished by using a coronary sinus lead (See U.S. Pat. No. 5,935,160, hereby incorporated by reference) with distal and proximal electrodes. The ventricle can be paced in accordance with a programmed pacing mode with the electrodes being energized simultaneously during each pacing output in order to achieve near simultaneous activation of the ventricle. Alternatively, the pacing stimuli can be delivered to the ventricular electrodes sequentially with a specified time delay in order to take into account differing conduction times within the ventricle.

In an exemplary embodiment of the invention described below with reference to the drawings, a capture verification test is performed by a multi-site pacemaker using a dedicated evoked response sensing channel. (As the term is used herein, the term "pacemaker" should be taken to mean any cardiac rhythm management device, such as an implantable cardioverter/defibrillator, with a pacing functionality.) In this test, it is determined whether or not a sensing/pacing channel is achieving capture with the pacing pulses delivered by the channel's electrode. The evoked response sensing channel includes a sense amplifier for sensing an evoked response generated after a pacing pulse is delivered. The evoked response sensing channel is connected to a selected electrode of the pacemaker's sensing/pacing channels by means of a switching circuit. After switching the input of the evoked response sensing channel to the electrode that is to be tested to verify capture, a pacing pulse is output and an evoked response is either detected or not, signifying the presence or loss of capture, respectively. Although the same electrode can be used for pacing and evoked response detection during a capture verification test, the input of the evoked response sensing channel preferably is switched to an electrode of another sensing/pacing channel. The particular electrode used for evoked response detection can be selected in accordance with which electrode is placed in a location where an evoked response due to the pacing electrode can be most easily sensed. The sense amplifier of the evoked response sensing channel is then blanked during the capture verification test for a specified blanking period following a pacing pulse output by the tested sensing/pacing channel. The blanking period is followed by a capture detection window during which an evoked response may be sensed by the evoked response sensing channel. In an exemplary embodiment, the blanking period may be approximately 10 ms, and the width of the capture detection window may range from 50 to 350 ms.

A block diagram of a multi-site pacemaker having an atrial and two ventricular pacing channels is shown in FIG. 1. The control unit of the pacemaker is made up of a microprocessor 10 communicating with a memory 12 via a bidirectional data bus 13, where the memory 12 typically comprises a ROM (read-only memory) for program storage and a RAM (random-access memory) for data storage. The control unit could be implemented by other types of logic circuitry (e.g., discrete components or programmable logic arrays) using a state machine type of design, but a microprocessor-based system is preferable. The control unit is capable of operating the pacemaker in a number of programmed modes where a programmed mode defines how pacing pulses are output in response to sensed events and expiration of time intervals. A telemetry interface 80 is also provided for communicating with an external programmer.

The pacemaker has an atrial sensing/pacing channel comprising ring electrode 43a, tip electrode 43b, sense amplifier 41, pulse generator 42, and an atrial channel interface 40 which communicates bidirectionally with a port of microprocessor 10. The device also has two ventricular sensing/pacing channels that similarly include ring electrodes 23a and 33b, tip electrodes 23b and 33b, sense amplifiers 21 and 31, pulse generators 22 and 32, and ventricular channel interfaces 20 and 30. The electrodes are electrically connected to the device by means of a lead (not shown). For each channel, the same lead and electrode are used for both sensing and pacing. The pacemaker also has an evoked response sensing channel that comprises an evoked response channel interface 50 and a sense amplifier 51. The channel interfaces include analog-to-digital converters for digitizing sensing signal inputs from the sensing amplifiers, registers that can be written to for adjusting the gain and threshold values of the sensing amplifiers, and, in the case of the ventricular and atrial channel interfaces, registers for controlling the output of pacing pulses and/or changing the pacing pulse amplitude.

Figure 2:
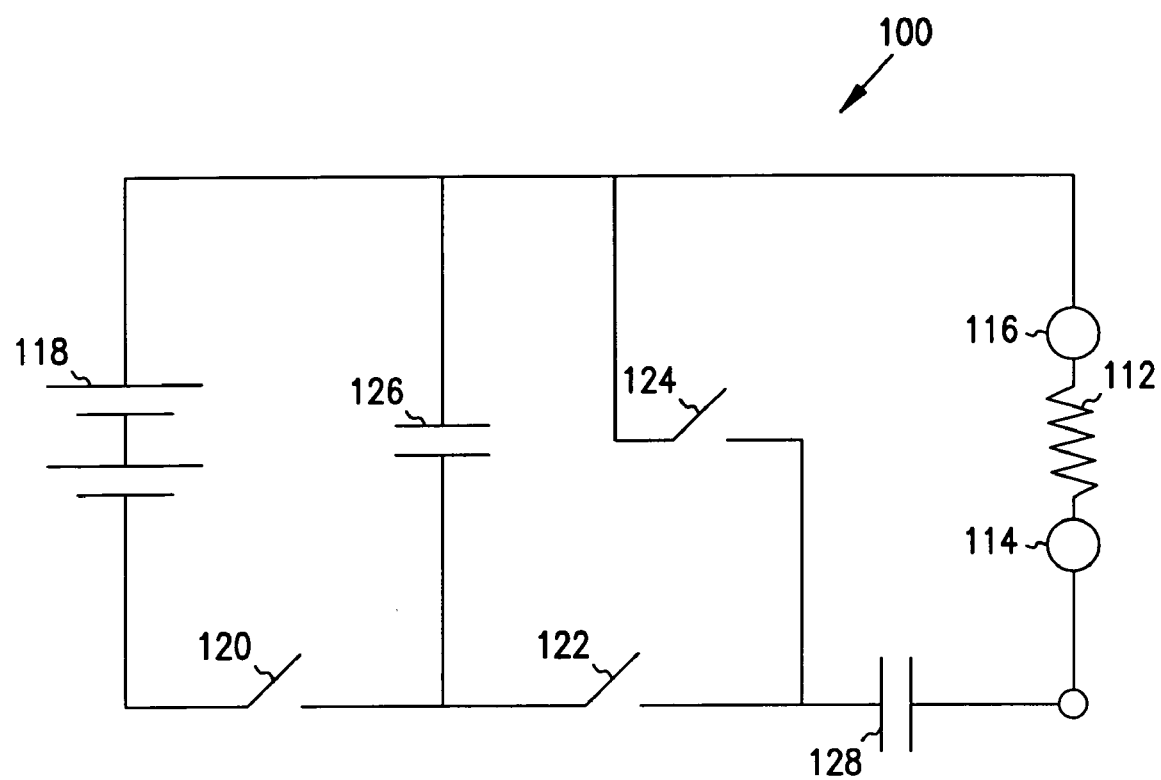
FIG. 2 is a schematic of a basic pulse generator.

FIG. 2 is a circuit diagram illustrating a conventional pacing output circuit 100 which is representative of the pulse generators 22, 32, or 42 in FIG. 1. The pacing output circuit 100 is designed to selectively generate and deliver stimulus pulses to the heart of a patient, indicated schematically as the resistive load 112, via a tip electrode 114 and ring electrode 116. The circuit 100 includes a power supply or battery 118, a first switch 120, a second switch 22, a third switch 124, a pacing charge storage capacitor 126, and a coupling capacitor 128, all of which operate under the direction of a microprocessor-based controller to perform a charging cycle, a pacing cycle, and a recharging cycle. The charging cycle involves closing the first switch 120 and opening the second and third switches 122, 124 such that the pacing charge storage capacitor 126 is charged up to a predetermined voltage level. The pacing cycle involves opening the first and third switches 120, 124 and closing the second switch 122 such that the voltage within the pacing charge storage capacitor 126 may be discharged through the coupling capacitor 128 to the tip electrode 114 of the pacemaker. Immediately after pacing, the second and third switches 122, 124 are opened and the charges within the coupling capacitor 128 will decay slowly through leakage. The recharging cycle involves opening the first and second switches 120 and 122 and closing the third switch 124 for a predetermined period of time following the pacing pulse to allow the coupling capacitor 128 to be discharged through the load 112. An improved version of the pulse generation circuit is described in U.S. Pat. No. 5,843,136, issued to Zhu, et. al, which is hereby incorporated by reference.

Figure 3:
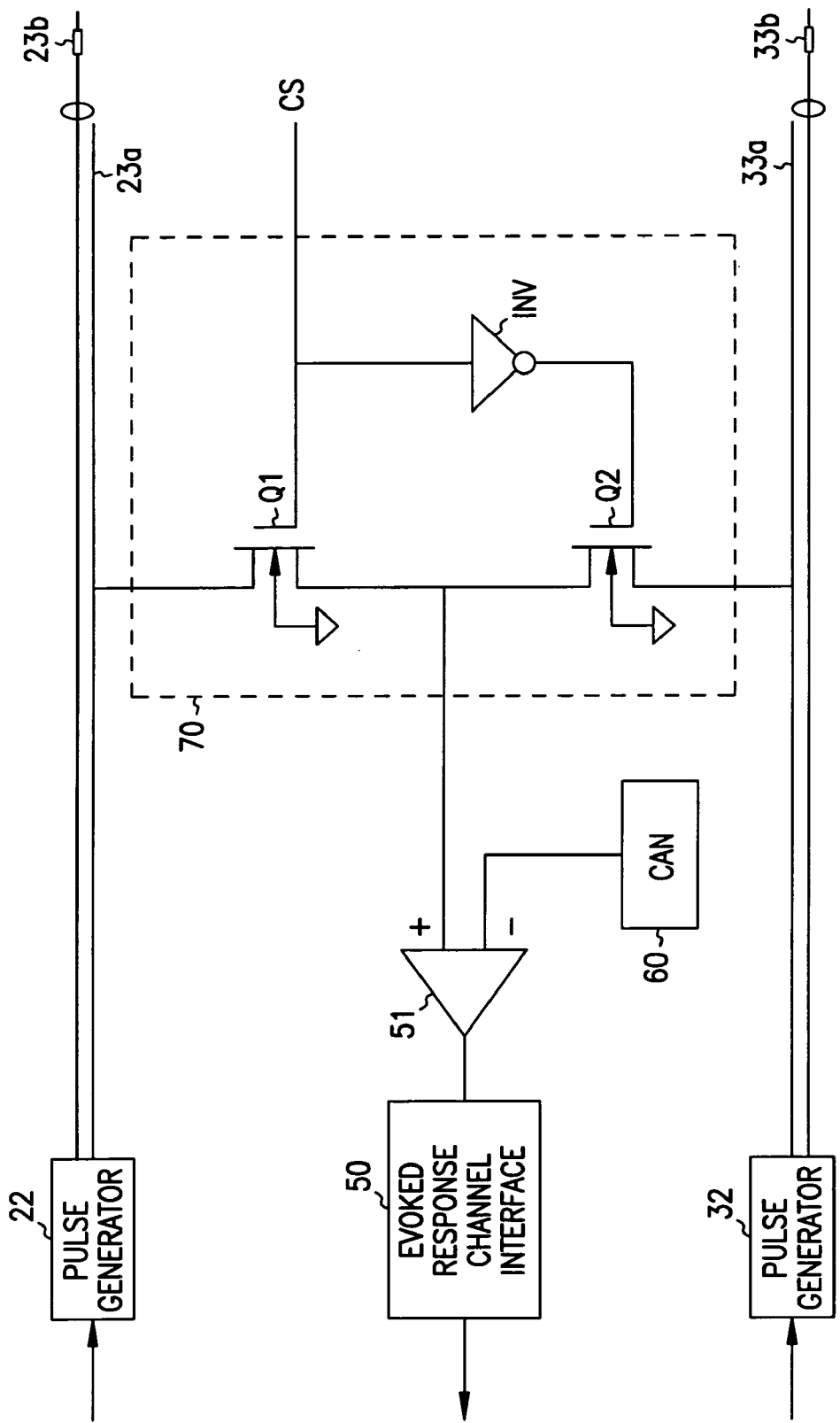
FIG. 3 is a diagram representing a portion of an exemplary switching circuit.

Referring back to FIG. 1, the electrodes are connected to the sense amplifiers by means of a switching circuit 70 which enables the amplifiers to be connected to selected tip or ring electrodes of any of the sensing/pacing channels that connect through the switching circuit 70. Each sense amplifier amplifies the voltage difference between two inputs, and the inputs may be selected from any of the tip or ring electrodes or the pacemaker case or can 60, which is also electrically connected to the switching circuit. The configuration of the switching circuit 70 is preferably implemented as an array of MOSFET transistors controlled by outputs of the controller 10. FIG. 3 shows a portion of a basic exemplary switching circuit. In this circuit, a pair of MOSFET transistors Q1 and Q2 along with inverter INV form a double-pole switch that switches one of the inputs to amplifier 51 between ring electrode 23a and 33a. The other input is shown as being connected to can 60, but in other embodiments it may also be switched to one of the electrodes by means of the switching circuit. In a more complicated version of the same basic pattern, the switching circuit 70 may be able to switch the inputs of the evoked response sensing channel to any of the tip or ring electrodes of the sensing/pacing channels or to the can 60.

In another aspect of the invention, a backup pacing pulse is delivered by the pacemaker during a capture verification test if a loss of capture is detected. In a multi-site pacemaker, the backup pulse can be delivered using a pacing channel other than the one that has just delivered a pulse that failed to achieve capture, where both channels are configured to pace either the ventricles or the atria. By using a separate pulse generator to output the backup pacing pulse, the backup pulse can be more efficiently delivered without the need for waiting for an output capacitor to recharge. In the biventricular pacemaker shown in FIG. 1, for example one of the ventricular sensing/pacing channels is used to sense the evoked response while the other ventricular channel delivers a pace. The channel used to sense the evoked response can also be used to provide backup pacing to the ventricle if capture is not achieved by the pace, with normal pacing by that channel preferably suspended.

The controller may also be programmed to implement an algorithm for determining the present pacing threshold of a pacing channel and adjusting a pacing parameter accordingly using the capture verification test as described. The steps of such an algorithm are as follows:

a) performing a capture verification test on the channel;
b) raising or lowering the pacing voltage by a specified amount if capture was present or absent, respectively, during the preceding capture verification test;
c) repeating the capture verification test with the raised or lowered pacing voltage;
d) determining the pacing threshold as the unraised pacing voltage if the pacing voltage was raised at step b and a loss of capture occurred during the repeated capture verification test, or repeating steps b through d otherwise.

The above-described threshold determination procedure may also be performed by adjusting the pulse width in addition to, or instead of, the voltage amplitude. The pacemaker controller may be programmed to perform the procedure, or individual capture verification tests on selected electrodes, at periodic intervals or in accordance with commands received via a telemetry link from an external programmer.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A cardiac pacemaker, comprising:
a plurality of electrodes disposable near a heart chamber;
a plurality of pacing channels, wherein each such channel includes a pulse generator connectable to a selected electrode;
a controller for controlling the operation of the pacemaker;
an evoked response sensing channel comprising a sense amplifier for sensing an evoked response generated after a pacing pulse;
a switching circuit operable by the controller for configuring a pacing channel or the evoked response sensing channel with a particular electrode;
a telemetry interface;
wherein the controller is programmed to perform a capture verification test upon receiving a command via the telemetry interface to test the sensing/pacing channel for presence or loss of capture, the capture verification test being performed by configuring the evoked response sensing channel with a particular electrode specified for the particular pacing channel to be tested via the switching circuit and sensing whether an evoked response occurs during a capture detection window following the output of a pacing pulse; and,
wherein the controller is programmed to determine a pacing threshold of a sensing/pacing channel upon receiving a command via the telemetry interface by:
a) performing a capture verification test on the channel;
b) lowering a pacing pulse energy by a specified amount if capture was present during the preceding capture verification test and raising a pacing pulse energy by a specified amount if capture was absent during the preceding capture verification test;
c) repeating the capture verification test with the raised or lowered pacing pulse energy; and,
d) determining the pacing threshold as the unlowered pacing pulse energy if the pacing pulse energy was lowered at step b and a loss of capture occurred during the repeated capture verification test, and repeating steps b through d otherwise.

2. The pacemaker of claim 1 comprising pacing channels for right and left ventricles, wherein the controller may be commanded via the telemetry interface to perform a capture verification test on either pacing channel.

3. The pacemaker of claim 1 wherein the input of the evoked potential sensing channel is switched to an electrode of a pacing channel other than the channel being tested during a capture verification test.

4. The pacemaker of claim 3 wherein the controller is programmed to output a backup pacing pulse through a pacing channel if loss of capture is detected during a capture verification test.

5. The pacemaker of claim 4 wherein the controller is programmed such that the backup pacing pulse is output through a pacing channel other than the channel being tested during the capture verification test.

6. The pacemaker of claim 1 wherein the controller is programmed to blank the sense amplifier of the evoked response sensing channel during the capture verification test for a specified blanking period following a pacing pulse output by the tested sensing/pacing channel, wherein the blanking period is followed by a capture detection window during which an evoked response may be sensed.

7. The pacemaker of claim 1 wherein the pacing pulse energy is raised and lowered by adjusting the duration of the pacing pulse.

8. The pacemaker of claim 1 wherein the pacing pulse energy is raised and lowered by adjusting the voltage amplitude of the pacing pulse.

9. The pacemaker of claim 1 wherein the pacemaker further comprises a plurality of pacing channels and wherein the controller is programmed to perform a pacing threshold determination on a selected pacing channel in accordance with commands received via a telemetry link from an external programmer.

10. The pacemaker of claim 1 wherein the pacemaker is programmed to perform a pacing threshold determination on the pacing channel at periodic intervals.

11. A method for determining a pacing threshold for a pacemaker having multiple pacing channels, comprising:
a) performing a capture verification test on a pacing channel by configuring an evoked response sensing channel with a particular electrode specified for the particular pacing channel to be tested via a switching circuit, outputting a pacing pulse through the pacing channel, and sensing whether an evoked response occurs during a capture detection window following the output of the pacing pulse via the evoked response sensing channel;
b) lowering a pacing pulse energy by a specified amount if capture was present during the preceding capture verification test and raising a pacing pulse energy by a specified amount if capture was absent during the preceding capture verification test;
c) repeating the capture verification test with the raised or lowered pacing pulse energy; and,
d) determining the pacing threshold as the unlowered pacing pulse energy if the pacing pulse energy was lowered at step b and a loss of capture occurred during the repeated capture verification test, and repeating steps b through d otherwise.

12. The method of claim 11 wherein the pacemaker is a biventricular device with at least two ventricular pacing channels and further comprising selecting one of the ventricular pacing channels for testing and switching the input of the evoked response sensing channel to an electrode of another ventricular sensing/pacing channel.

13. The method of claim 11 wherein the input of the evoked potential sensing channel is switched to an electrode of a sensing or pacing channel other than the channel being tested during a capture verification test.

14. The method of claim 13 further comprising outputting a backup pacing pulse through a pacing channel if loss of capture is detected during a capture verification test.

15. The method of claim 14 wherein the backup pacing pulse is output through a pacing channel other than the channel being tested during the capture verification test.

16. The method of claim 11 further comprising blanking a sense amplifier of the evoked response sensing channel during the capture verification test for a specified blanking period following a pacing pulse output by the tested pacing channel, wherein the blanking period is followed by a capture detection window during which an evoked response may be sensed.

17. The method of claim 11 wherein the pacing pulse energy is raised and lowered by adjusting the duration of the pacing pulse.

18. The method of claim 11 wherein the pacing pulse energy is raised and lowered by adjusting the voltage amplitude of the pacing pulse.

19. The method of claim 11 further comprising performing a pacing threshold determination on a selected channel at periodic intervals.

20. The method of claim 11 further comprising performing a pacing threshold determination on a selected channel in accordance with commands received via a telemetry link from an external programmer.

* * * * *

UNITED STATES PATENT AND TRADEMARK OFFICE
CERTIFICATE OF CORRECTION

PATENT NO.       : 7,623,921 B2                                    Page 1 of 1
APPLICATION NO.  : 11/210143
DATED            : November 24, 2009
INVENTOR(S)      : Russie et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 326 days.

Signed and Sealed this

Twenty-sixth Day of October, 2010

David J. Kappos
*Director of the United States Patent and Trademark Office*